United States Patent [19]
McKinley et al.

[11] Patent Number: 5,457,880
[45] Date of Patent: Oct. 17, 1995

[54] EMBEDDED FEATURES FOR MONITORING ELECTRONICS ASSEMBLY MANUFACTURING PROCESSES

[75] Inventors: Philip E. McKinley, Westford; Carl J. Bloch, Wayland, both of Mass.; Ramaswamy Ranganathan, Cupertino, Calif.

[73] Assignee: Digital Equipment Corporation, Maynard, Mass.

[21] Appl. No.: 193,330

[22] Filed: Feb. 8, 1994

[51] Int. Cl.⁶ .................................................. H05K 3/30
[52] U.S. Cl. ............................. 29/833; 29/834; 29/840; 228/56.3; 437/8
[58] Field of Search ...................... 29/834, 833, 843; 228/56.3; 437/8

[56] References Cited

U.S. PATENT DOCUMENTS

| | | | |
|---|---|---|---|
| 3,796,497 | 3/1974 | Mathisen et al. | 356/152 |
| 4,005,939 | 2/1977 | Stavalone | 356/165 |
| 4,291,334 | 9/1981 | Mese et al. | 358/101 |
| 4,463,310 | 7/1984 | Whitley | 324/73 PC |
| 4,655,600 | 4/1987 | Tanigawa | 356/401 |
| 4,796,560 | 1/1989 | Berger et al. | |
| 4,866,837 | 9/1989 | Heissenberger et al. | 29/833 X |
| 4,985,107 | 1/1991 | Conroy et al. | 156/299 |
| 5,017,514 | 5/1991 | Nishimoto | 437/229 |
| 5,022,580 | 6/1991 | Pedder | 29/834 X |
| 5,153,507 | 10/1992 | Fong et al. | 437/8 X |
| 5,153,678 | 10/1992 | Ota | 356/401 |
| 5,195,279 | 3/1993 | Wern | 51/415 |
| 5,201,452 | 4/1993 | Takahashi et al. | |
| 5,323,947 | 6/1994 | Juskey et al. | 228/56.3 |

FOREIGN PATENT DOCUMENTS 3-214790   9/1991   Japan ..................................... 29/843

OTHER PUBLICATIONS

J. Electronic Packaging and Production vol. 29 No. 1 pp. 42–44 Jan. 1989 by Von Voss et al.

Microelectronic Packaging Technology, Materials and Processes, Proc. of 2nd ASM Intr Electronic Materials & Processing Congress pp. 281–293, Apr. 24–28, 1989 Shieh (Editor), Paper by Dody.

*Primary Examiner*—Carl J. Arbes
*Attorney, Agent, or Firm*—James F. Thompson; Ronald C. Hudgens

[57] ABSTRACT

Cooperative patterns are formed in stencils and/or substrates that facilitate the monitoring and control of the circuit assembly process. A pattern of successively-larger etch blocks receives a corresponding pattern of same-size solder blocks; solder reflow problems are indicated when either too many or too few etch blocks are completely covered by solder after reflow. A pattern of same-size etch blocks receives a corresponding pattern of successively-larger solder blocks; problems with solder stencil clogging are indicated when smaller ones of the etch blocks do not receive solder paste during stenciling. Finally, component beacon openings or translucent areas are made in the electronics assembly at component locations. After component placement, the board is appropriately lit, and any uncovered openings indicate missing or grossly misaligned components.

3 Claims, 3 Drawing Sheets

EMBEDDED FEATURES FOR MONITORING ELECTRONICS ASSEMBLY MANUFACTURING PROCESSES

FIELD OF THE INVENTION

The invention is related to the field of electronics assembly manufacturing, such as the assembly of components onto printed circuit boards.

BACKGROUND OF THE INVENTION

In the field of electronics assembly manufacturing, it is often necessary to monitor work pieces at a particular manufacturing stage, in order to determine qualitatively or quantitatively how a process used at that stage is performing. One example of such a process is the process of soldering components to a PC board. During a conventional PC board soldering process, a solder stencil is placed over a component-connection surface of a PC board. The solder stencil has numerous openings corresponding to locations where solder paste is to be placed, such as contact pads that will subsequently receive component leads. After the solder stencil has been placed, solder paste is deposited over it. Then the solder stencil is removed, leaving the PC board stenciled with numerous blocks of solder paste on its surface. Once the board has been stenciled in this fashion, the components are placed on the board, and the assembly is heated to reflow the solder, thereby completing the connection between the components and the board.

In the foregoing soldering process, it is necessary to monitor how well the solder "wets" or covers its associated pads and component leads. Poor wetting in particular can be problematic, as it may contribute to defective solder joints between the component and the board. Poor wetting may be caused by a variety of factors, such as improper oven temperature or poor solder paste quality, for example. Another potential problem is the tendency of the solder stencil to become clogged with solder as it is used repetitively. As a stencil becomes clogged, less solder is deposited on the board; this may also contribute to defective solder joints. For these reasons, then, monitoring of the soldering process is essential to achieving good PC board yields.

Another example of monitoring an electronics assembly manufacturing process is the monitoring of electronic component placement. Since much of present-day placement is performed automatically, it is necessary to monitor the performance of placement equipment so that adjustments can be made if necessary. In particular, monitoring may involve determining whether all the necessary components have been attached to a given PC board, and whether they are correctly aligned with interconnection pads on the board so that good electrical contact is assured.

A common method of carrying out necessary process monitoring is to visually inspect the boards upon completion of the process step being monitored. To monitor the degree of solder wetting, for example, a technician might examine a board in several places, looking for evidence of insufficient wetting. This process is tedious, error-prone, and time-consuming, and does not necessarily yield consistent results. Improved methods of inspection are therefore desirable that can be performed as quickly and robustly as possible, so that effective monitoring is obtained at a minimum cost.

SUMMARY OF THE INVENTION

It is an object of the invention to effect the above-described process monitoring in a manner that is robust, yet simple and inexpensive. The present invention has several aspects that contribute to achieving this objective.

In a first aspect, the invention is a method of fabricating an electronics assembly with solderability-monitoring features, the method including the steps of: (i) forming an array of solderability-monitoring pads on a component-connection layer of the electronics assembly, each of the solderability-monitoring pads being of successively greater area; (ii) forming an array of solderability-monitoring openings in a solder stencil associated with the component-connection layer of the electronics assembly, the solderability-monitoring openings being of equal size and slightly smaller than the smallest of the solderability-monitoring pads, the solderability-monitoring openings being located on the solder stencil such that when the solder stencil is placed in a registered position on the component-connection layer of the electronics assembly, each of the solderability-monitoring openings is substantially centered on a corresponding one of the solderability-monitoring pads; (iii) placing the solder stencil on the component-connection layer of the electronics assembly in the neighborhood of the registered position; (iv) depositing solder paste on the electronics assembly through the solder stencil; (v) removing the solder stencil from the electronics assembly; (vi) placing components on the component-connection layer of the electronics assembly; (vii) reflowing the electronics assembly to solder the components to the component-connection layer; and (viii) examining the solderability-monitoring pads to detect changes in solder wetting of the electronics assembly, decreased wetting being indicated when the number of the solderability-monitoring pads that are completely covered by reflowed solder is less than the number of completely-covered pads on other electronics assemblies recently fabricated by the same fabrication process, and increased wetting being indicated when the number of the solderability-monitoring pads that are completely covered by reflowed solder is greater than the number of completely-covered pads on other electronics assemblies recently fabricated by the same fabrication process.

This first aspect of the invention provides a simple way to determine the quality of reflow without having to inspect component-connection pads that are partially or fully covered by corresponding component leads.

In a second aspect, the invention addresses the problem of solder stencil clogging. It is a method of fabricating an electronics assembly using features to monitor stencil clogging, the method including the steps of: (i) forming a set of clog-monitoring openings in a solder stencil associated with a component-connection layer of the electronics assembly, each of the clog-monitoring openings being of successively greater area in a range between a smallest area smaller than a smallest component-connection opening in the solder stencil and a largest area larger than the smallest component-connection opening; (ii) forming upon the component-connection layer of the electronics assembly a set of clog-monitoring pads of equal size slightly larger than the largest of the clog-monitoring openings in the solder stencil, the clog-monitoring pads being located on the electronics assembly such that when the solder stencil is placed in a registered position on the component-connection layer of the electronics assembly, each of the clog-monitoring openings is substantially centered on a corresponding one of the clog-monitoring pads; (iii) placing the solder stencil on the component-connection layer of the electronics assembly in the neighborhood of the registered position; (iv) depositing solder paste on the electronics assembly through the solder stencil; (v) removing the solder stencil from the electronics assembly; and (vi) examining the clog-monitoring pads to determine the degree of clogging of the solder stencil, an acceptable degree of clogging being indicated when no more than a predetermined number of the smallest of the clog-monitoring pads have no solder paste thereon, and unacceptable clogging being indicated otherwise.

This second aspect of the invention provides an indication of stencil clogging directly on the electronics assembly that is to be inspected. The clog-monitoring features can be designed to detect clogging before it significantly affects the quality of the stenciling process, so that the stencil can be cleaned or replaced before adversely affecting electronics assembly yield.

In a third aspect, the invention addresses the problem of detecting missing or misplaced components. It is a method of fabricating a printed circuit board including the steps of: (i) forming component beacon openings in an otherwise substantially opaque layer of the electronics assembly, each component beacon opening being aligned with a placement site where an electronic component is to be placed and being sufficiently small to be covered by the electronic component; (ii) placing components on the electronics assembly; (iii) lighting the electronics assembly in a manner effective to highlight any of the component beacons not covered by their corresponding electronic components; and (iv) examining the electronics assembly to find uncovered ones of the component beacons, each uncovered one indicating that its corresponding electronic component has not been correctly placed on the electronics assembly.

The component beacons simplify the process of visual inspection of the electronics assembly and give a clear indication of missing components, thus increasing the quality of the inspection process.

All these and other features and advantages of the present invention will be apparent from the following detailed description.

BRIEF DESCRIPTION OF THE DRAWINGS

Specific embodiments of the invention will be described with reference to the accompanying drawings, in which.

DETAILED DESCRIPTION

Figure 1:
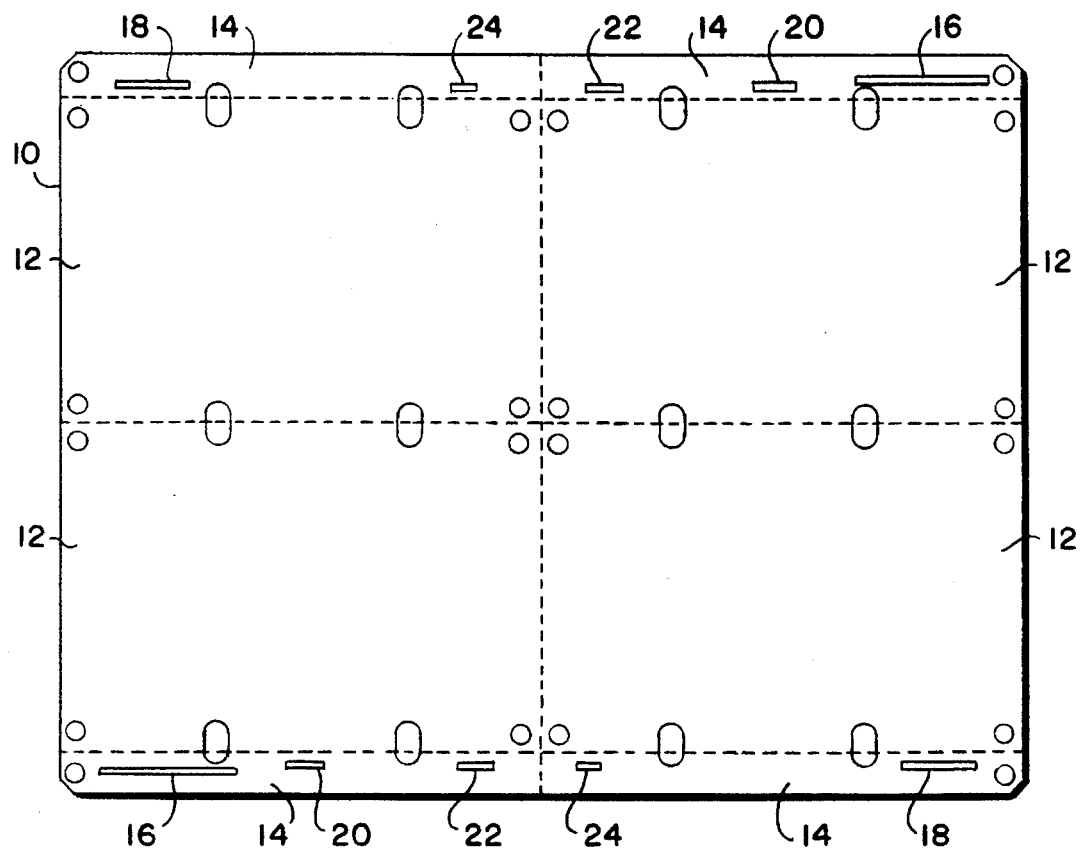
FIG. 1 is a schematic diagram of a printed circuit board incorporating the principles of the present invention.
Figure 2:
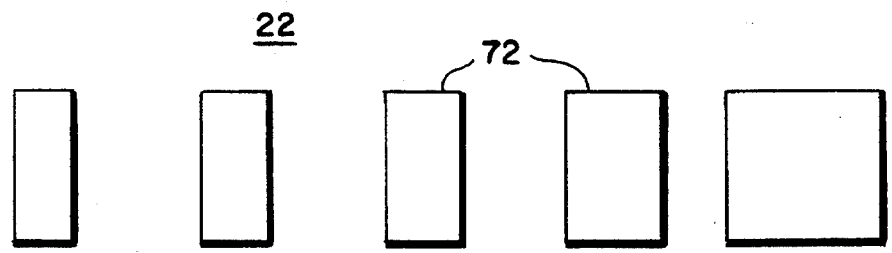
FIG. 2 shows a portion of the circuit board of FIG. 1 having a pattern of etch used for monitoring the solderability of the circuit board.
Figure 3:
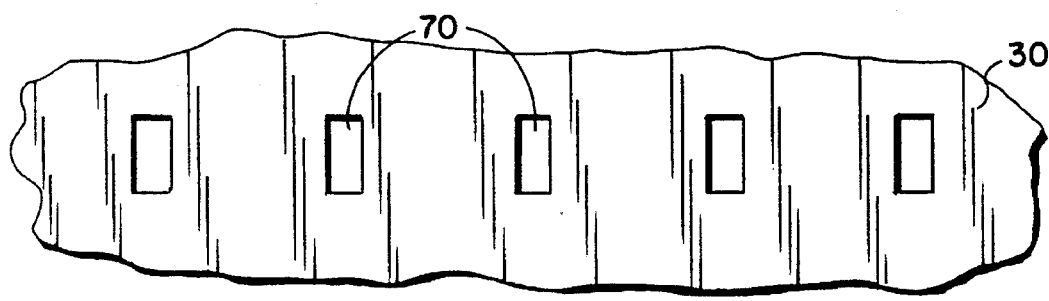
FIG. 3 shows a portion of a solder stencil having openings for forming a pattern of solder paste blocks to be used with the pattern of FIG. 2 for monitoring the solderability of the circuit board.
Figure 4:
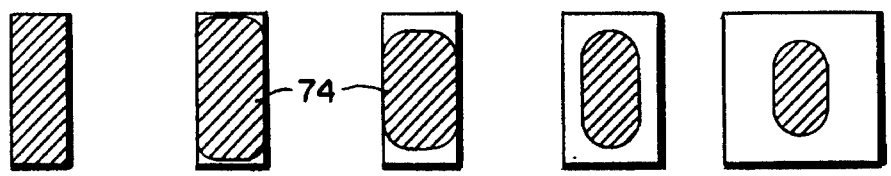
FIG. 4 shows the circuit board of FIG. 2 after reflow with an intermediate degree of solder wetting.
Figure 5:
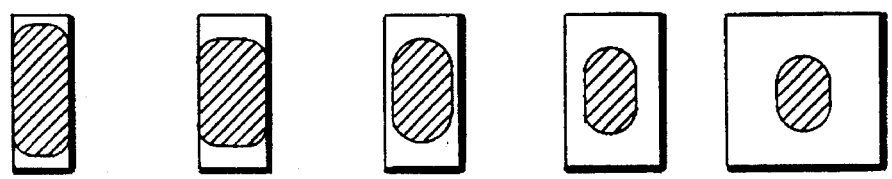
FIG. 5 shows the circuit board of FIG. 2 after reflow with a smaller degree of solder wetting.
Figure 6:
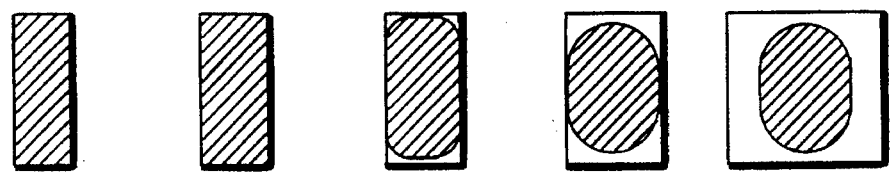
FIG. 6 shows the circuit board of FIG. 2 after reflow with a greater degree of solder wetting.

FIG. 1 shows a printed circuit (PC) board 10 as it exists during the manufacturing process. The illustrated PC board 10 is approximately 6 by 8 inches, and actually consists of 4 identical circuit portions 12. During the manufacturing process, these circuit portions 12 are separated so that each becomes a separate finished printed circuit. Although they are not shown in FIG. 1, it is to be understood that each circuit portion 12 has a number of component-connection pads to which the leads of electronic components are to be soldered during the manufacturing process. The PC board 10 also has tab portions 14 that are used only during the manufacturing process; during a later manufacturing step they are separated from the circuit portions 12 and discarded.

The tab portions 14 have several patterns of etch deposited thereon that are used for monitoring various manufacturing steps. The locations of these patterns are shown in FIG. 1, while the detailed appearance of each pattern is shown in subsequent Figures. There are (i) a first vernier alignment pattern 16; (ii) a second vernier alignment pattern 18; (iii) an angled bar alignment pattern 20; (iv) a solderability monitoring pattern 22; and (v) a solder stencil clog monitoring pattern 24. In the illustrated embodiment, the vernier alignment patterns 16 and 18 are used to monitor the horizontal alignment of solder paste to the PC board 10; the angled bar pattern 20 is used to monitor the vertical alignment of the solder paste; the solderability monitoring pattern 22 is used to monitor the quality of the solder joints formed by the soldering process; and the stencil clog monitoring pattern 24 is used to determine whether solder paste deposition is being hindered by clogging of the openings on the solder stencil.

While the locations of the monitoring patterns shown in FIG. 1 are particularly suitable for the illustrated PC board 10, it will be clear to those skilled in the art that the patterns may advantageously be placed at other locations. For example, the definitions of "horizontal" and "vertical" are arbitrary; the patterns could readily be employed at the lateral edges of the PC board 10 rather than the upper and lower edges. Alternatively, the patterns may be located on the circuit portions 12 rather than on separable portions such as tab portions 14.

It will be readily understood by those skilled in the art that the PC board 10 has associated therewith a solder stencil that is used to mask portions of the PC board 10 during a conventional manufacturing step of depositing solder paste in preparation for soldering electronic components to the PC board 10. Such a solder stencil has component-connection openings in locations corresponding to the component-connection pads on the PC board 10. The openings allow the deposition of solder paste on the connection pads, while the body of the stencil prevents such deposition elsewhere on the PC board 10. It is to this step of masked solder paste deposition that several aspects of the present invention are directed.

In FIGS. 2 through 6, the solderability monitoring pattern 22 of FIG. 1 is described. In the solder stencil 30, a set of solderability-monitoring openings 70 are formed; in the illustrated embodiment, these are 10×20 mils in size and have 50 mil pitch. Corresponding solderability-monitoring pads 72 are formed on the PC board 10 of FIG. 1. The solderability-monitoring pads 72 are of successively greater area as shown. In the illustrated embodiment, the pads 72 are all 40 mils high, have 50 mil pitch, and have respective widths of 16, 18, 21, 26 and 40 mils.

During the soldering process, blocks of solder paste 74 are deposited onto the pads 72, and the panel is reflowed in a conventional fashion. After reflow, the spread of the solder paste blocks 74 across their corresponding pads 72 is observed. The solderability-monitoring features do not necessarily give an absolute indication of reflow quality; rather, they enable changes in reflow characteristics to be detected. For example, during a given interval the reflow process might consistently yield a pattern like that shown in FIG. 4. If reflow wetting performance should change, then patterns like those shown in FIGS. 5 and 6 may result, wherein wetting has either diminished or increased. These changes can be caused by a variety of factors, such as oven temperature, metal surface characteristics, and solder paste quantity and quality. The solderability-monitoring pattern 22, then, is an easily-used indicator of solder wetting, and may obviate a much more time-consuming, detailed inspection of the board.

It should be noted that for the solderability-monitoring pattern 22 to be useful, the pads 72 must contrast with the solder blocks 74. Bare copper or nickel-gold pads 72 are therefore preferred when conventional tin/lead-based solder is used.

Figure 9:
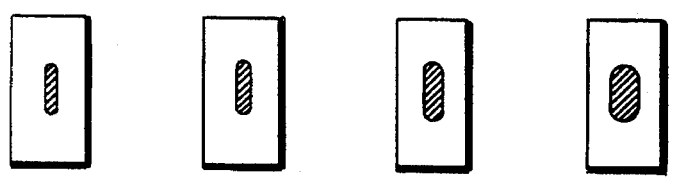
FIG. 9 shows the circuit board of FIG. 7 after solder paste stenciling when the solder stencil is partially clogged.
Figure 7:
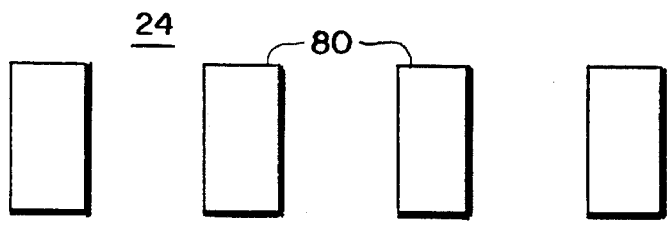
FIG. 7 shows another portion of the circuit board of FIG. 1 having a pattern of etch used for monitoring the clogging tendency of openings in an associated soldering stencil.
Figure 8:
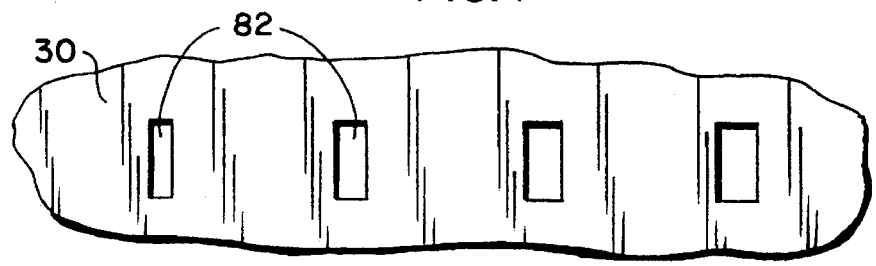
FIG. 8 shows a portion of a solder stencil having openings for forming a pattern of solder paste blocks to be used with the pattern of FIG. 7 for monitoring solder stencil clogging.

FIGS. 7 through 9 illustrate another aspect of the present invention, namely the stencil clog monitoring pattern 24. A set of equal-size clog-monitoring pads 80 is formed on the PC board 10 of FIG. 1. In the illustrated embodiment, these pads 80 are 40×80 mils and have 50 mils pitch. Clog-monitoring openings 82 are made in the stencil 30. The openings 82 are of successively greater area as shown. In the illustrated embodiment, these openings are all 20 mils high and have 50 mil pitch, and have respective widths of 6, 8, 10, and 12 mils. Repeated clog monitoring patterns can be used throughout the area printed to increase the monitoring coverage and observable sample size.

As the solder stencil 30 is used during solder paste stenciling, the smaller ones of the openings 82 may become clogged with solder paste. When solder paste is subsequently deposited onto the PC board 10, the pads 80 corresponding to these clogged openings will not have any solder paste deposited onto them. By monitoring which, if any, of the pads 80 lack solder paste, the degree of clogging of the stencil 30 can be ascertained. It is preferable that the sizes of the openings 82 be in a range about the smallest component-connection opening in the stencil 30, so that clogging which could affect such an opening can be readily detected.

Figure 10:
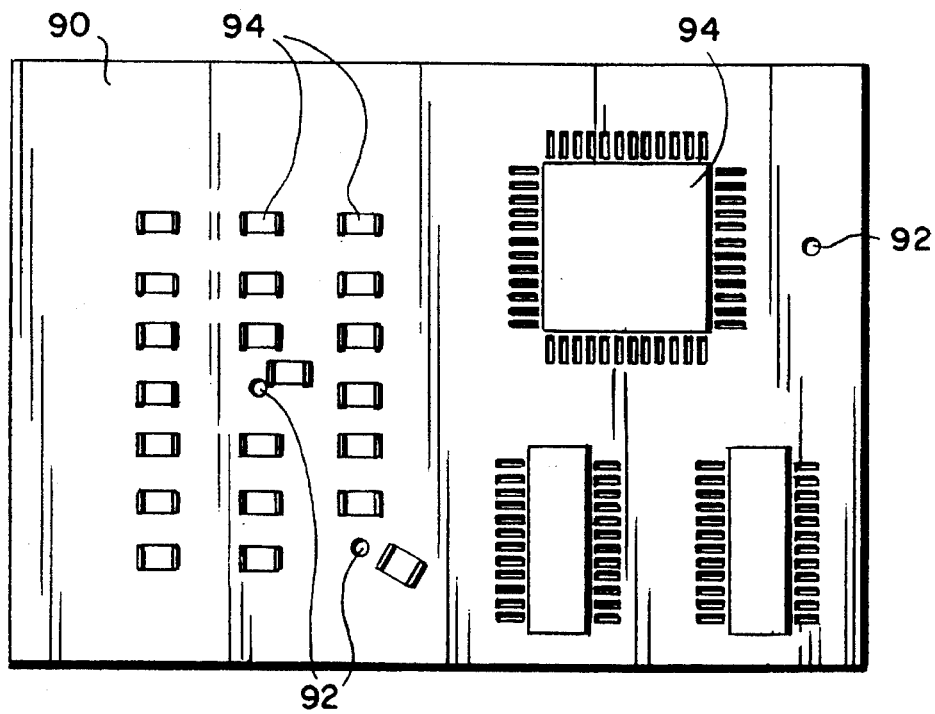
FIG. 10 is a diagram of a circuit board having missing component beacons in accordance with the principles of the present invention.

FIG. 10 shows another printed circuit board 90 that embodies another aspect of the present invention. A number of component beacon openings 92 have been made in one layer of the board 90 that is otherwise substantially opaque, such as an inner reference or mask layer. Each opening 92 must pass light through the board 90, so none of the other layers should block the openings 92. Each opening 92 is directly underneath a corresponding one of the components 94 that populate the board 90, and is small enough to be covered thereby. The exact size of a given opening 92 therefore depends on the size of the corresponding component. Generally, larger holes are preferred for ease of detection. After component placement has occurred, either before or after soldering, the board 90 is back-lit to highlight any uncovered openings 92. An uncovered opening 92 indicates that the corresponding component is either completely missing or substantially misaligned. This procedure provides a simple, inexpensive method to monitor the performance of automatic placement equipment. It should also be noted that smaller components in particular benefit from the presence of the beacons, because their presence or absence is less readily detected by more conventional means.

A variation of the idea of missing component beacons accommodates different versions of a board 90 that use some different components. In such a case, some components 94 may be correctly missing from one version of the board 90, so it would be undesirable to flag them as erroneously missing components. In such a case, it may be advantageous to employ openings of a different shape beneath such optional components. For example, there could be square openings beneath the components 94 required by all versions, and triangular openings under those components only required by a particular version. An uncovered triangular opening would only indicate a problem during the assembly of that particular version. Such a scheme is of course extendable to other shapes and to many versions, and could also be used with machine vision systems as well as with human operators.

What has been described is a set of embedded features to assist in the monitoring and control of assembly processes for electronic components such as printed circuit boards. While these features in all their detail embody the present invention, other embodiments exist as well that are intended to be described by the following claims.

What is claimed is:

1. A method of fabricating an electronics assembly, comprising the steps of:

forming an array of solderability-monitoring pads on a component-connection layer of said electronics assembly, each of said solderability-monitoring pads being of successively greater area;

forming an array of solderability-monitoring openings in a solder stencil associated with said component-connection layer of said electronics assembly, said solderability-monitoring openings being of equal size and slightly smaller than the smallest of said solderability-monitoring pads, said solderability-monitoring openings being located on said solder stencil such that when said solder stencil is placed in a registered position on said component-connection layer of said electronics assembly, each of said solderability-monitoring openings is substantially centered on a corresponding one of said solderability-monitoring pads;

placing said solder stencil on said component-connection layer of said electronics assembly in the neighborhood of said registered position;

depositing solder paste on said electronics assembly through said solder stencil;

removing said solder stencil from said electronics assembly;

placing components on said component-connection layer of said electronics assembly;

reflowing said electronics assembly to solder said components to said component-connection layer; and examining said solderability-monitoring pads to detect changes in solder wetting of said electronics assembly, decreased wetting being indicated when the number of said solderability-monitoring pads that are completely covered by reflowed solder is less than the number of completely-covered pads on other electronics assemblies recently fabricated by the same fabrication process, and increased wetting being indicated when the number of said solderability-monitoring pads that are completely covered by reflowed solder is greater than the number of completely-covered pads on other electronics assemblies recently fabricated by the same fabrication process.

2. A method of fabricating an electronics assembly, comprising the steps of:

forming a set of clog-monitoring openings in a solder stencil associated with a component-connection layer of said electronics assembly, each of said clog-monitoring openings being of successively greater area in a range between a smallest area smaller than a smallest component-connection opening in said solder stencil and a largest area larger than said smallest component-connection opening;

forming upon said component-connection layer of said electronics assembly a set of clog-monitoring pads of equal size slightly larger than the largest of said clog-monitoring openings in said solder stencil, said clog-monitoring pads being located on said electronics assembly such that when said solder stencil is placed in a registered position on said component-connection layer of said electronics assembly, each of said clog-monitoring openings is substantially centered on a corresponding one of said clog-monitoring pads;

placing said solder stencil on said component-connection layer of said electronics assembly in the neighborhood of said registered position;

depositing solder paste on said electronics assembly through said solder stencil;

removing said solder stencil from said electronics assembly; and examining said clog-monitoring pads to determine the degree of clogging of said solder stencil, an acceptable degree of clogging being indicated when no more than a predetermined number of the smallest of said clog-monitoring pads have no solder paste thereon, and unacceptable clogging being indicated otherwise.

3. A method of fabricating an electronics assembly, comprising the steps of:

forming component beacon openings in an otherwise substantially opaque layer of said electronics assembly, each component beacon opening being aligned with a placement site where an electronic component is to be placed and being sufficiently small to be covered by said electronic component;

placing components on said electronics assembly;

lighting said electronics assembly in a manner effective to highlight any of said component beacons not covered by their corresponding electronic components; and examining said electronics assembly to find uncovered ones of said component beacons, each uncovered one indicating that its corresponding electronic component has not been correctly placed on said electronics assembly.

* * * * *